US005458593A

United States Patent [19]

Macabasco et al.

[11] Patent Number: 5,458,593

[45] Date of Patent: Oct. 17, 1995

[54] DOCKABLE BAG SYSTEM AND METHOD

[75] Inventors: Agilio E. Macabasco; Renato R. Salumbides, both of San Dimas, Calif.

[73] Assignee: Bayer Corporation, Berkeley, Calif.

[21] Appl. No.: 157,686

[22] Filed: Nov. 24, 1993

[51] Int. Cl.[6] .......... A61M 1/32

[52] U.S. Cl. .......... 604/403; 604/408; 604/410; 128/DIG. 24

[58] Field of Search .......... 604/403, 408, 604/409, 410; 206/438, 570, 571, 484, 524.2, 524.3, 524.9, 524.6; 128/DIG. 24; 220/403, 419, 450

[56] References Cited

U.S. PATENT DOCUMENTS 4,381,776 5/1983 Latham, Jr. .......... 604/408
4,976,707 12/1990 Bodicky et al. .......... 604/410

FOREIGN PATENT DOCUMENTS 8808694 11/1988 WIPO .......... 604/408

*Primary Examiner*—Randall L. Green
*Assistant Examiner*—P. Zuttarelli
*Attorney, Agent, or Firm*—Elizabeth F. Enayati

[57] ABSTRACT

Apparatus and method for sterile docking two or more plastic bag units 110. The invention generally includes a sterilizable pouch 102 manufactured from an essentially vapor transmission resistant material. Contained within the pouch 102 is at least one plastic bag unit 110 and a predetermined amount of sterile tubing 108 connected thereto. The pouch 102 includes an aperture 104 in one wall or at one seam through which a tube fitting 106 protrudes. The tube fitting 106 has an internal diameter sufficient to permit passage therethrough of the tubing 108 contained within the pouch 102 and connected to the bag unit 110 contained therein. The protruding tubing 108 then may be used for docking with other bag units 110.

8 Claims, 3 Drawing Sheets

DOCKABLE BAG SYSTEM AND METHOD

BACKGROUND OF THE INVENTION

1. Field of the Invention

The present invention generally relates to the field of blood bag systems, and specifically relates to the field of sterile docking multiple blood bag systems.

2. Description of Related Art

Plastic bag systems for the collection, processing, and storage of blood and blood components are well known and have been used for thirty or more years. In early embodiments, when plastic films were used to make bags that ultimately replaced glass bottles, many of the plastic blood bag systems were "open" in the sense that there existed the chance of contamination as blood or separated blood components were moved into or out of the system. Quite often, the plastic bag system was a single bag having attached to it one or more tubings and ports for adding or removing bag contents.

As the use of various components and sub-components of blood became accepted, attempts were made to avoid potential contamination problems by providing multiple blood bags attached to each other by tubings and including valving systems. These multiple blood bag systems are known as "closed" in the sense that there no longer exists the chance of contamination after whole blood or a major component is introduced into and processed in the system.

Depending on design, the number of bags, and such factors as valving systems and internal solutions, there now exists a variety of closed multiple blood bag systems. Available systems permit the collection, processing and storage of well known blood components such as red cell concentrates, plasma, and platelets.

Blood bags most often are manufactured from plastics such as polyvinylester, polyvinyl acetates, polyolefin, polyvinylchloride homopolymer films, and the like. These materials tend to have a high water vapor transmission rate such that the bag has to be in an aluminum foil pouch to assure a longer shelf life of any solution contained in the bag. Not only do solutions contained within the bags become dehydrated, but the condensation on the outside of the bags resulting from the vapor transmission promotes bacteria growth.

Existing blood bag systems frequently are packaged within aluminum foil pouches to reduce the amount of vapor transmission. Typically, blood bags are sterilized, placed inside an aluminum foil pouch, sealed, and then heat treated. However, to make a sterile docking to another system, the pouch must be opened to access the tubing contained within the bag. The combined blood bag systems then are repackaged in a single pouch for storage. Unfortunately, this method of docking multiple blood bag systems reduces the shelf life of the blood bag units. Furthermore, the possibility of mold growth in the blood bag system is increased due to the handling of the individual units and the necessary exposure of the individual systems to the environment.

Thus, there remains a need for an apparatus for sterile docking multiple blood bag systems without exposing the systems to handling and environmental contamination.

SUMMARY OF THE INVENTION

The present invention is an apparatus and method for sterile docking two or more plastic bag units 110. The invention generally includes a pouch 102 manufactured from an essentially vapor transmission resistant material. Contained within the pouch 102 is at least one plastic bag unit 110 and a predetermined amount of sterile tubing 108 connected thereto.

The pouch 102 includes an aperture 104 in one wall or at one seam through which a tube fitting 106 protrudes. Preferably, the fitting 106 is sonic welded in place in the aperture 104 to form a hermetic seal. The tube fitting 106 has an internal diameter sufficient to permit passage therethrough of the tubing 108 contained within the pouch 102 and connected to the bag unit 110 contained therein. The protruding tubing 108 then may be used for docking with other bag units 110.

In a preferred form of the invention, the plastic bags 110 are blood bags that form part of a blood bag system. More specifically, the plastic bag system is a blood bag system, having at least one blood bag unit and an amount of flexible tubing, and the plastic bag unit 110 is a blood bag unit that contains a solution including anticoagulant, saline, and the like for use in conjunction with collected blood.

DESCRIPTION OF THE PREFERRED EMBODIMENTS

The present invention is a system 100 for sterile docking plastic bags 110 contained within a vapor transmission containment pouch. In a preferred form of the invention, the system 100 is used for sterile docking multiple blood bag units 110, at least one of such units 110 being contained within the inventive system 100.

Figure 1:
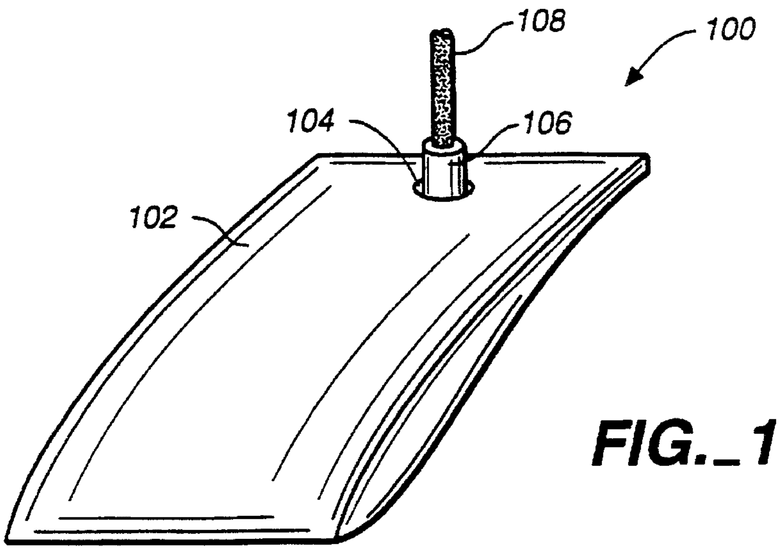
FIG. 1 is a perspective view of an embodiment of the present invention.

FIG. 1 shows a perspective view of one embodiment of the present system 100. In that illustrated embodiment, the system 100 includes a pouch 102 of sufficient size and dimensions to hold a bag unit (110 of FIG. 2). The illustrated pouch 102 is sealed at all edges such that the contents of the pouch are maintained in an air-tight environment.

Preferably, the pouch 102 is manufactured from a material that may be sterilized, either by heat (e.g., autoclave), chemical, radiation, or other standard methods known and used in the art. The material preferably is vapor transmission resistant; that is, the material does not transmit water, in vapor form, to outside of the pouch from inside the pouch. Preferably, the moisture transmission value of the pouch material is zero or as close to zero as possible. In a preferred embodiment of the present invention, the pouch 102 is manufactured using an aluminum foil laminate, which has a known water transmission rate of zero.

One of the advantages of using aluminum foil as a pouch material is that it has the lowest water vapor transmission rate of other materials, it is low cost, and it is generally commercially available. In a preferred form of the invention, the pouch 102 is constructed from a laminate that includes an outer layer of a polyester film, a middle layer of annealed aluminum foil, an inner layer of polyethylene or polypropylene, and an intermediate tie layer of polyethylene copolymer of FDA approved adhesive. Alternatively, the intermediate tie layer may be an extrusion laminated seal layer. Foil material is commercially available from several suppliers, including American National Co., Mt. Vernon, Ohio.

The inventive system 100 further includes an aperture 104 or other opening in the pouch 102 through which a tube fitting 106 protrudes. The aperture 104 may be located either in one of the walls of the pouch 102 (as illustrated in FIG. 1), or may be formed at one of the pouch 102 seams. In a preferred embodiment, the aperture 104 is positioned in one of the pouch 102 walls and proximal one end of the pouch 102. The position of the aperture 104 may depend on such variables as the position of the bag unit 110 within the pouch 102, the amount of tubing 108 to be threaded through the fitting 106, and other manufacturing and assembly considerations.

The plastic bag unit 110 contained within the pouch 102 preferably is sterilizable. Standard sterilizing methods, such as heat, chemical, radiation, and the like, may be used on the bag units 110 prior to insertion of the bag units 110 inside the pouch 102. Presterilization of the bag units 110 may further extend the shelf-life of the bag 110 contents.

Figure 2:
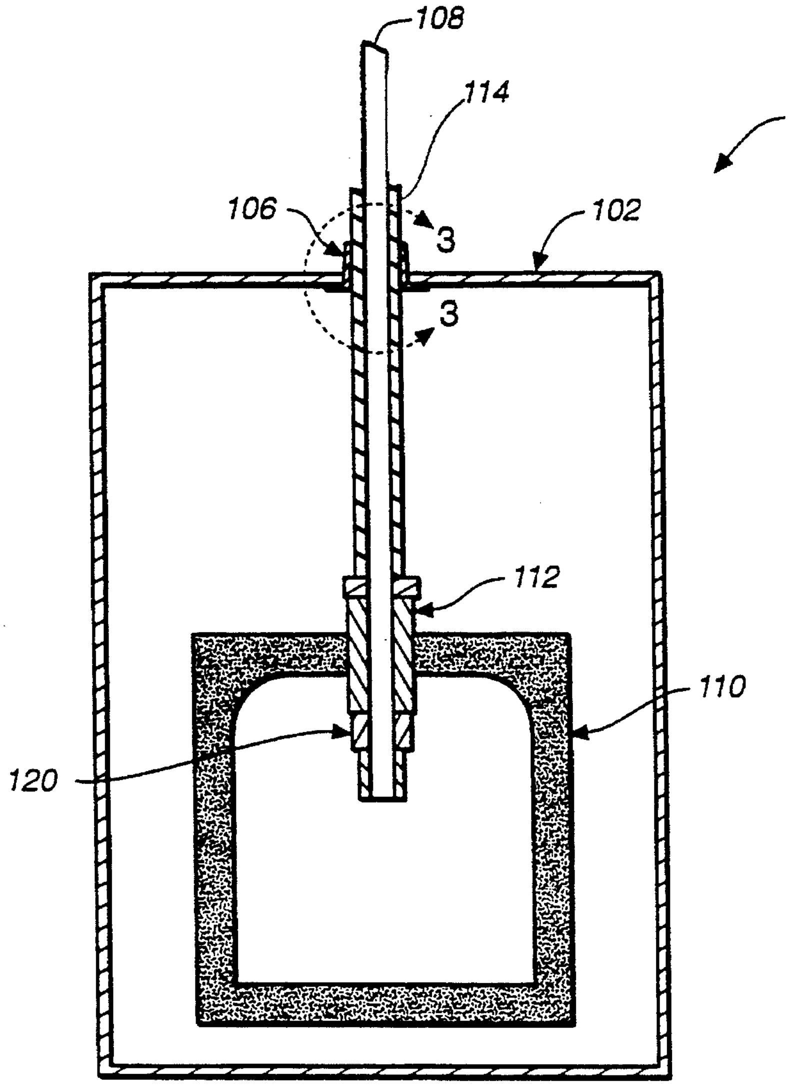
FIG. 2 is a front cutaway view of an embodiment of the present invention.

Turning now to FIG. 2, that shows a front cutaway view of the present system 100. In that illustrated embodiment, the system 100 includes a plastic bag 110 contained within the pouch 102. The plastic bag 110 may be a blood bag, manufactured from standard materials used in the blood bag industry. Such bags 110 are commercially available from Miles Inc., Covina, Calif. The bag 110 may contain a solution for transfer to another system 100, a blood collection system, another plastic bag, and the like. The present invention is particularly suited for sterile docking of the plastic bag 110 to another sterile system.

The bag 110 of the illustrated system may include a port 112, attached to the bag 110, that has an attached amount of tubing 108 that extends from the contents of the bag 110 to outside the system 100. A standard frangible valve 120 may be positioned within the port to control flow of fluid from the bag 110 to outside of the system 100 via the tubing 108.

In the illustrated embodiment, a bushing 114 is attached to the bag port 112 and extends at least partially through the aperture 104. The bushing 114 may extend beyond the fitting 106, and acts as a conduit for the tubing 108. In an alternative embodiment of the invention, the tubing 108 extends directly from the bag 110 through the fitting 106 without the guidance of a bushing 114.

Figure 3:
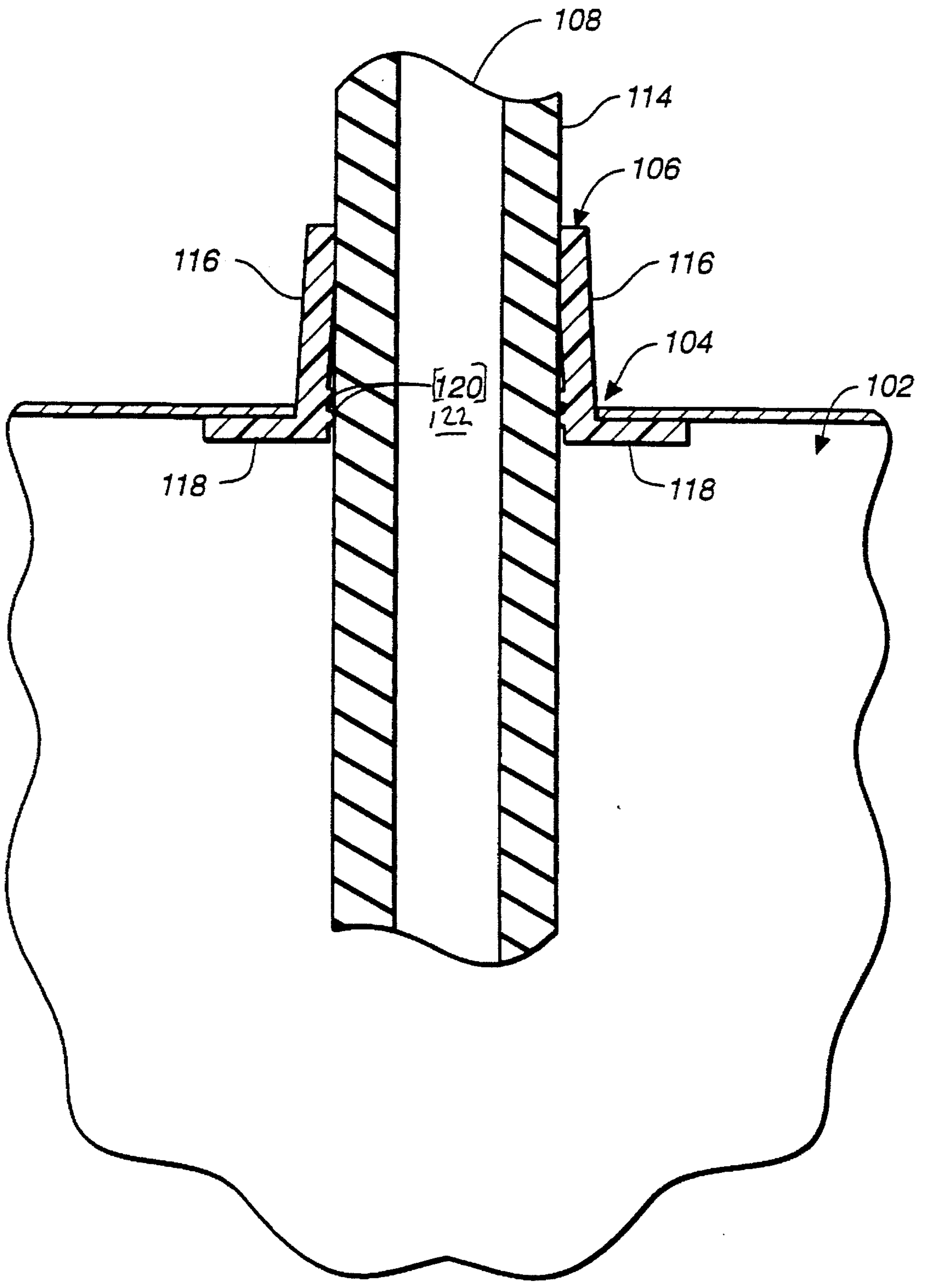
FIG. 3 is a detail cross-section of a fitting used in an embodiment of the present invention.

In a preferred embodiment of the invention, and as shown in detail in FIG. 3, the tubing fitting 106 includes a main body portion 116 and a foot portion 118. In assembling the illustrated embodiment of the invention, the fitting body 116 is inserted through the aperture 104 from the inside of the pouch 102 such that the body 116 protrudes from within the pouch 102 and the foot portion 118 abuts against the inner pouch surface adjacent the aperture 104. The fitting 106 may then be welded or otherwise attached to the pouch 102.

In the illustrated embodiment, the fitting body 116 includes a pair of flanges 122 that extend around the circumference of the inner side of the body 116. The flanges 122 function to grip the bushing 114, or tubing 108 when no bushing 114 is present, to further secure the bushing 114 or tubing 108 in position within the fitting 106.

In a preferred form of the invention, the fitting 106 is sonically welded to the pouch 102 to form a hermetic seal. In alternative forms of the invention, the fitting 106 is attached within the aperture 104 by chemical, RF, or other methods known and available to those skilled in the art. Preferably, any method that produces a hermetic seal may be used to secure the fitting 106 to the pouch 102.

In one embodiment of the present invention, the terminal end of tubing 108 that extends outside of the pouch 102 is sealed. Preferably, the seal is an RF seal, but the manner and type of seal may depend on the specific materials from which the tubing is manufactured. It is desirable that the terminal end of the tubing 108 be sealed or otherwise closed to prevent uncontrolled loss of solution from the bag 110 and to prevent introduction of contaminants into the bag 110.

Figure 4:
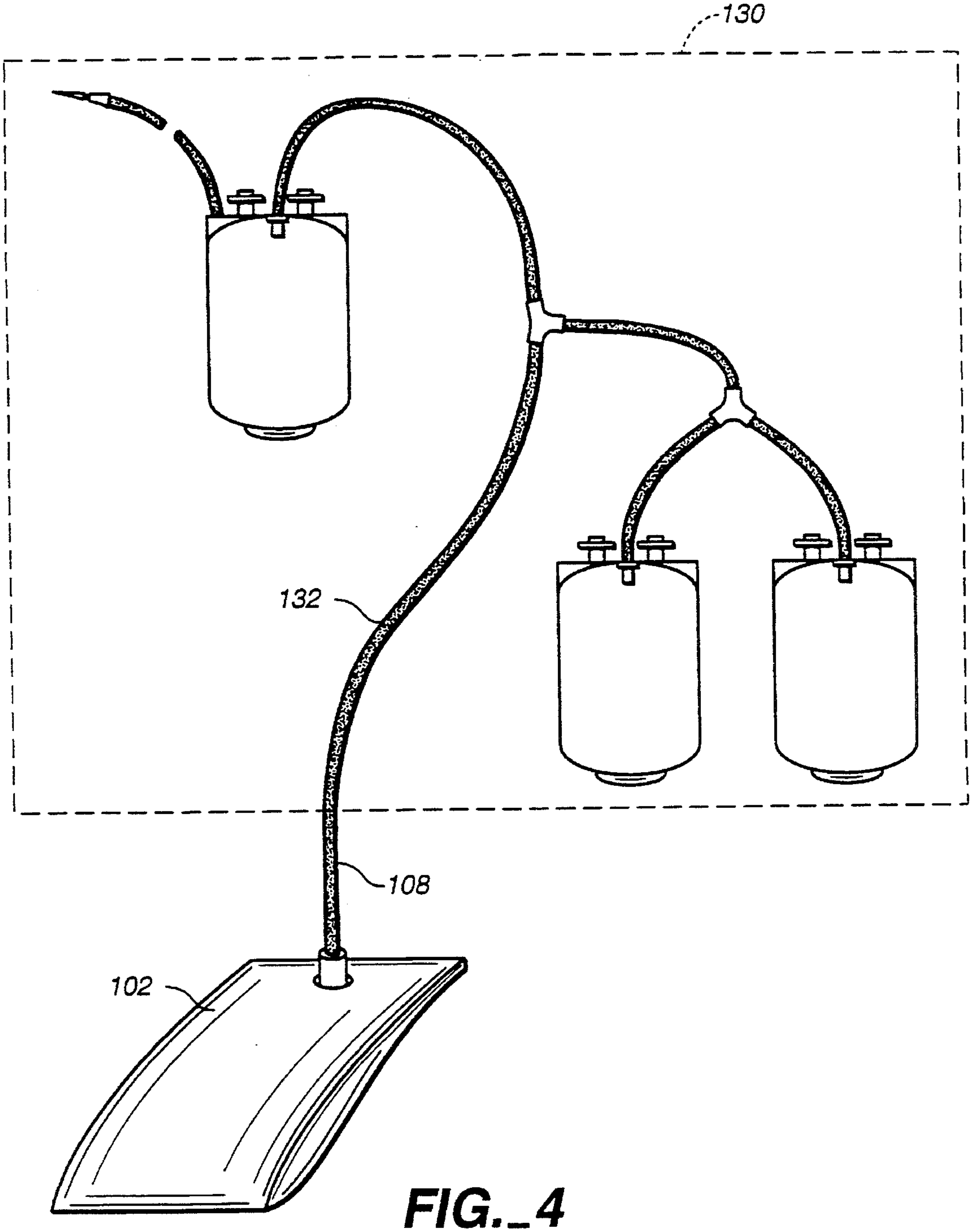
FIG. 4 is a perspective view of an exemplary configuration using an embodiment of the present invention.

In practicing the present invention, and referring to FIG. 4, the portion of the tubing 108 that extends outside of the pouch 102 is connected to tubing 132 from another system 130. The system 130 may include a blood bag system, as illustrated in FIG. 4, another single blood bag unit 110 similar to that shown in FIG. 2, or the like. In a preferred method of practicing the present invention, sterile docking is accomplished using a sterile docking device, such as that commercially available from DuPont, Wilmington, Del. Using that exemplary device, the two tubings 108 and 132 to be joined are positioned in the docking device (not shown). The device cuts the tubing ends. The opened ends then are joined automatically, typically using a heat process. Once the system 100 is sterile docked, the frangible valve 112, if present, may be opened to permit fluid flow from the bag 110 to the sterile docked system 130. That device is described in further detail in U.S. Pat. No. 4,507,119, the relevant portions of which are incorporated herein by reference. Another sterile docking device is described in U.S. Pat. No. 4,157,123, and which relevant portions thereof also are incorporated herein by reference.

In one embodiment of the present invention, a single blood bag unit 110 is sealed within the pouch 102. In alternative embodiments, the pouch 102 includes two or more bags, each of which may be interconnected via tubing, or may have separate lengths of tubing extending outside of the pouch 102. In a preferred form of the invention, a previously sterilized plasma collection bag, including a tubing harness, and containing a sterilized solution for long-term storage is placed in the pouch 102.

An exemplary system and use are demonstrated below.

EXAMPLE

A 200 ml blood bag 110 containing an amount of anticoagulant citrate phosphate double dextrose solution (CP2D), obtained from Miles Inc., Covina, Calif., is placed within an aluminum foil pouch 102 made of a laminate substantially as described above. The foil pouch 102 includes an aperture 104 punched into one pouch wall approximately 5 cm from the top edge of the pouch 102. A flanged fitting 106, preferably manufactured from polyethylene or polypropylene is positioned within the aperture 104 and sonically welded into position.

The blood bag 110 includes a frangible valve closure 120, to which is connected a length of PVC tubing. Preferably the tubing is not less than 12 inches in length. The exact length of tubing may be longer, depending on the type of sterile docking device being used. That tubing 108 is threaded through the flanged fitting 106 from inside the bag 110 such that it extends at least about 1 cm above the fitting 106. The system 100 now is ready to for long-term storage and/or sterile docking with another blood bag system.

The above description is included to illustrate the preferred embodiments and the operation of the preferred embodiments and is not meant to limit the scope of the invention. The scope of the invention is to be limited only by the following claims. From the above discussion, many variations will be apparent to one skilled in the art that would yet be encompassed by the spirit and scope of the invention.

What we claim is:

1. Apparatus for sterile docking a plurality of flexible bag units, comprising:

A. a sealed, closed pouch manufactured from vapor transmission resistant material;

B. a bag system contained within the closed pouch, including at least one bag unit and an amount of flexible tubing connected thereto; and C. at least one external tube fitting attached to and protruding through one side of the closed pouch and having an amount of the flexible tubing extending therethrough.

2. The apparatus of claim 1, wherein the tube fitting is sonic welded to one side of the closed pouch.

3. The apparatus of claim 1, wherein at least one bag unit contains a quantity of a sterile solution.

4. The apparatus of claim 1, wherein the tube fitting is hermetically sealed to one side of the closed pouch.

5. The apparatus of claim 1, wherein the vapor transmission resistant material comprises an aluminum foil.

6. The apparatus of claim 1, wherein the bag system comprises a blood bag system.

7. The apparatus of claim 1, wherein the bag unit comprises a blood bag unit.

8. The apparatus of claim 1, wherein the external tube fitting includes at least one flange therewithin for securing the flexible tubing therein.

* * * * *